(12) United States Patent
Frigg et al.

(10) Patent No.: US 6,206,881 B1
(45) Date of Patent: *Mar. 27, 2001

(54) BONE PLATE

(75) Inventors: Robert Frigg, Davos Platz; Robert Schavan, Davos Dorf; Markus Hehli, Davos Frauenkirch, all of (CH)

(73) Assignee: Synthes (USA), Paoli, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,343

(22) PCT Filed: Sep. 6, 1995

(86) PCT No.: PCT/EP95/03494

§ 371 Date: Feb. 27, 1998

§ 102(e) Date: Feb. 27, 1998

(87) PCT Pub. No.: WO97/09000

PCT Pub. Date: Mar. 13, 1997

(51) Int. Cl.[7] .................................................. A61B 17/80
(52) U.S. Cl. ............................. 606/69; 606/73; 606/76; 606/70
(58) Field of Search .................................. 623/16, 16.11, 623/17.17, 17.18, 17.19; 606/69–72

(56) References Cited

U.S. PATENT DOCUMENTS

| 3,596,656 | 8/1971 | Kaute | ........................ 128/92 |
|---|---|---|---|
| 4,338,926 | * 7/1982 | Kummer et al. | ........................ 606/72 |
| 5,108,399 | * 4/1992 | Eitenmuller et al. | .................... 623/16 |
| 5,259,398 | * 11/1993 | Vrespa | ...................... 623/16 |
| 5,275,601 | * 1/1994 | Gogolewski et al. | .................. 606/72 |
| 5,487,741 | * 1/1996 | Maruyama et al. | ................... 606/60 |
| 5,534,027 | * 7/1996 | Hodorek | ................... 623/16 |
| 5,683,460 | * 11/1997 | Persoons | ................... 623/16 |
| 5,863,201 | * 1/1999 | Lazzara et al. | ........................ 623/16 |

FOREIGN PATENT DOCUMENTS

| 43 41 980 A1 | 6/1995 | (DE) . |
|---|---|---|
| 43 43 117 A1 | 6/1995 | (DE) . |
| 0 486 762 A1 | 5/1992 | (EP) . |
| 2 667 913 | 4/1992 | (FR) . |
| 2 706 763 | 12/1994 | (FR) . |
| WO 90/07304 | 7/1990 | (WO) . |

* cited by examiner

Primary Examiner—David H. Willse
Assistant Examiner—Suzette J. Jackson
(74) Attorney, Agent, or Firm—Pennie & Edmonds LLP

(57) ABSTRACT

A bone plating system for the internal stabilization of a fractured bone is disclosed. The system includes a bone plate having a plurality of conical plate holes tapering toward a bone contact surface and at least two bone screws for anchoring the bone plate to a bone. The screws have a conical head with a textured or structured lateral outside surface which is greater in hardness than the portion of the bone plate which is proximal to the plate holes. The present system provides positive locking between the screw heads and the plate holes.

19 Claims, 2 Drawing Sheets

BONE PLATE

FIELD OF THE INVENTION

The invention concerns a bone plate for internal stabilization of a fractured bone.

BACKGROUND

A bone plate of this general type is known from the European patent document A 0,530,585. The permanent affixation of bone plates with conical plate holes using bones screws with structured conical heads depends on the achievable geometric, i.e. positive locking between the screw heads and the plate holes, and such locking is most problematic when dealing with small sizes,

SUMMARY OF THE INVENTION

An object of the invention is to provide a bone plate of the above species ensuring optimal geometric locking using the bone screws used in affixing such bone plates.

The system according to the present invention comprises a bone plate with a plurality of conical plate holes tapering toward a bone contact surface and at least two bone screws for anchoring the bone plate to a bone. The screws have a conical head with a textured or structured lateral outside surface having a hardness which is greater than that of the portion of the bone plate proximal to the plate holes. Preferably, the hardness of the lateral outside surface is 230 to 450 HV and the hardness of the bone plate is 100 to 220 HV. The heads of the bone screws and the plate holes can both be fitted with threads. The threads can be mutually matching threads or the thread on the heads of the bone screws can comprise one or more turns relative to the thread of the plate holes.

In one embodiment, the structured lateral outside surface comprises a structure, preferably circumferential ribs, running transversely to the longitudinal axis of the bone screw. Preferably, the bone plate is made of a plastic and the screws are made of metal or ceramics. The plastic used for the bone plate can be reinforced with metal fibers, plastic fibers, or carbon fibers.

The advantages offered by the invention substantially are that, due to the design of the invention of the structured surfaces of the screw heads serving to affix the bone plate, excellent geometric locking with this plate is achieved.

The invention and further embodiments of this invention are elucidated below in relation to partly schematic representations of several illustrative embodiments, wherein:

DETAILED DESCRIPTION OF THE PREFERRED EMBODIMENT

Figure 1:
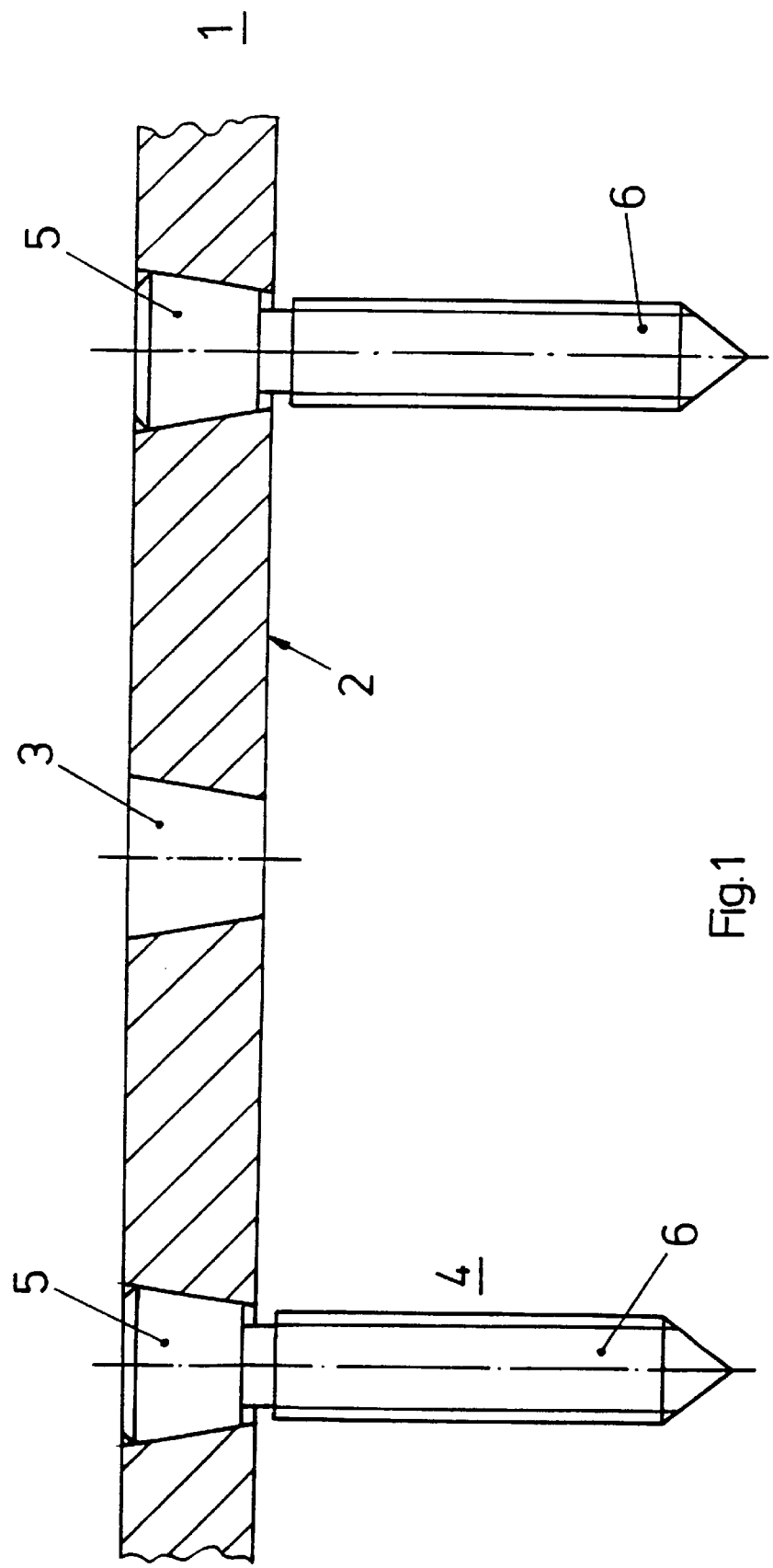
FIG. 1 is a longitudinal section through a bone plate according to the invention.
Figure 2:
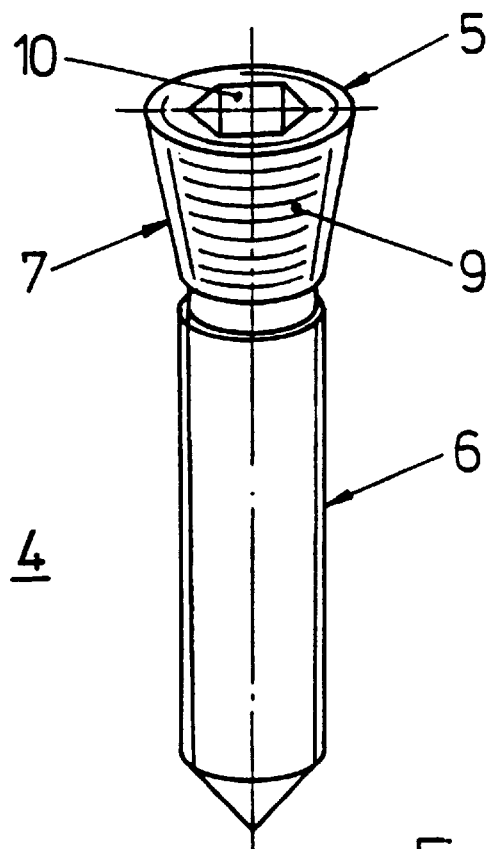
FIG. 2 is a perspective view of a bone screw for affixing the bone plate of FIG. 1.
Figure 3:
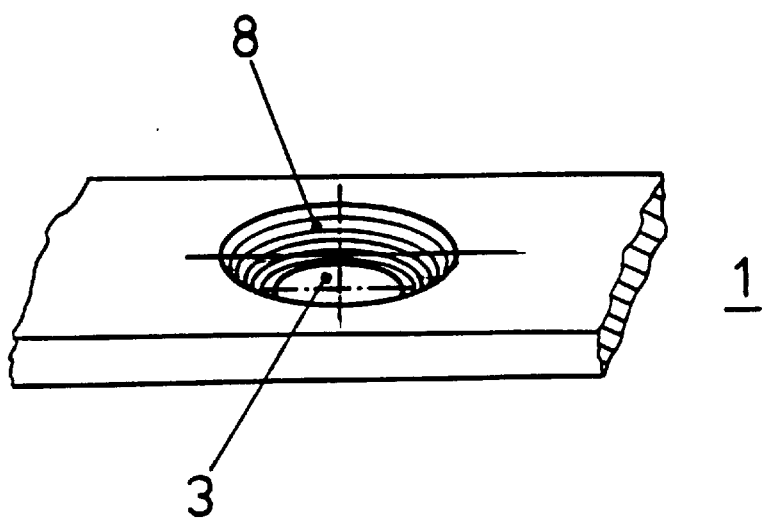
FIG. 3 is a partial perspective view of the top surface of the bone plate of FIG. 1.

The bone plate 1 shown in FIGS. 1 through 3 comprises several plate holes 3, each hole being shaped so that it tapers toward a bone contact surface 2 and receives bone screws 4. The bone screws 4 are formed with conical heads 5 having structured or textured lateral surfaces 7 for inserting these screws into conical plate holes 3 to which they are matched and also with threads 6 for anchoring into the bone.

The structured lateral surface 7 of head 5 of each bone screw 4 has greater hardness than the material in the vicinity of plate holes 3 in bone plate 1. As a result, even when bone screws 4 are inserted in an imperfectly coaxial manner into plate holes 3, optimal geometric locking is achieved because the harder, structured lateral surface 7 is able to penetrate the softer material of plate hole 3.

The hardness of the structured lateral outside surface 7 advantageously is selected in the range of 230 to 450 HV (Vickers hardness) and preferably in the range of 250 to 350 HV. A suitable material for the bone plate 1 is a metal with a hardness of 100 to 220, preferably 120 to 200 HV. Advantageously, the hardness of the structured lateral outside surface 7 is at least twice the hardness of the bone plate 1, preferably in the vicinity of its plate holes 3.

Preferably the structured lateral surface 7 is structured transversely to the longitudinal axis of the bone screw 4, for instance in the form of circumferential ribs. This feature improves geometrical locking.

In a preferred embodiment of the invention such as shown in FIG. 2, the lateral surface 7 of head 5 of a bone screw 4 is fitted with a thread 9 or with spiral structures.

As shown in FIG. 3, plate holes 3 also may be fitted with threads 8. Advantageously, the two threads 8 and 9 will match one another. Advantageously, in such a combination threads 9 of heads 5 of bone screws 4 will have two or more turns engaging threads 8 of plate holes 3.

At its top free end, head 5 of each bone screw comprises a hexagonal recess 10 to receive a hexagonal socket wrench.

Instead of making the head 5 of the bone screw 4 totally of a material which is harder than the bone plate 1, the head alternatively may be merely fitted with a coating having a greater hardness than bone plate 1 in the vicinity of plate holes 3. This coating may have a surface hardness of 500 to 10,000 and preferably between 1,000 and 5,000 HV.

Preferably, bone plate 1 is made of a plastic and bone screws 4 are made of metal or a ceramic. In particular, plastics, whether reinforced or not, of the following types are suitable for the bone plate:

polyacrylic ether ketone (PEAK) or polyether ether ketone (PEEK) with a rupture elongation of 40 to 70% and a Young's modulus of 3,000 to 6,000 N/mm$^2$;

polysulfone with a rupture elongation of 80 to 120% and a Young's modulus of 2,000 to 3,500 N/mm$^2$, Liquid Crystal Polymer (LCP) with a rupture elongation of 1.5 to 2.5% and a Young's modulus of 5,000 to 20,000 N/mm$^2$, polyoxymethylene (POM) with a rupture elongation of 10 to 50% and a Young's modulus of 2,00 to 3,500 N/mm$^2$, polyphenylene sulfide (PPS) with a rupture elongation of 0.2 to 1.0% and a Young's modulus of 12,000 to 20,000 N/mm$^2$.

The plastic may be reinforced by embedding metal fibers, plastic fibers or carbon fibers into the plastic matrix.

What is claimed is:

1. A system for fixation of bone fragments comprising a bone plate made of a non-resorbable polymer material with a plurality of conical plate holes each defined by a plate hole surface tapering toward a bone contact surface and at least two bone screws for anchoring the bone plate to a bone, each said screw having a conical head with a structured lateral outside surface, said head shaped to match the plate holes and used in insertion into said holes, the bone screws further comprising a threaded shank for anchoring into the bone, wherein the structured lateral outside surface of each conical screw head has a greater hardness than each plate hole surface so that insertion of the bone screws into the plate holes at other than a coaxial position still allows geometric locking to be achieved between each screw and plate hole by penetration of the respective plate hole surface by the harder structured lateral outside surface of the conical screw head.

2. A system for fixation of bone fragments comprising a bone plate made of a non-resorbable material with a plurality of conical plate holes tapering toward a bone contact surface and at least two bone screws for anchoring the bone plate to a bone, each said screw having a conical head with a structured lateral outside surface, said head shaped to match the plate holes and used in insertion into said holes, the bone screws further comprising a threaded shank for anchoring into the bone, wherein the bone plate is made of a metal having a hardness of 100 to 220 HV, the structured lateral outside surface has a hardness of 230 to 450 HV, and wherein insertion of the bone screws into the plate holes at other than a coaxial position still allows geometric locking to be achieved between each screw and plate hole by penetration of the respective plate hole surface by the harder structured lateral outside surface of the conical screw head.

3. The system of claim 2 wherein the lateral outside surface of the head of the bone screws is fitted with a spiral structure and the bone plate metal has a hardness of 120 to 200 HV.

4. The system of claim 3 wherein the plate holes are fitted with a thread and the hardness of the structured lateral outside surface is 250 to 350 HV.

5. A system for fixation of bone fragments comprising a bone plate with a plurality of conical plate holes tapering toward a bone contact surface and at least two bone screws for anchoring the bone plate to a bone, each said screw having a conical head with a structured lateral outside surface, said head shaped to match the plate holes and used in insertion into said holes, the bone screws further comprising a threaded shank for anchoring into the bone, wherein the structured lateral outside surface has a greater hardness than portions of the bone plate located adjacent the conical plate holes, and wherein the head of the bone screws is fitted with a coating of higher hardness than the portions of the bone plate adjacent the conical plate holes.

6. The system of claim 5, wherein the bone screw head coating has a surface hardness of 500 to 10,000 HV.

7. The system of claim 2 wherein the hardness of the structured lateral outside surface is at least twice the hardness of the bone plate.

8. The system of claim 1, wherein the structured lateral outside surface of the head of the bone screws and the plate holes have mutually matching threads.

9. The system of claim 4, wherein the lateral outside surface of the head is fitted with a thread, said thread comprises one or more turns relative to the thread of the plate holes.

10. The system of claim 1 wherein the structured lateral outside surface comprises a structure running transversely to a longitudinal axis of the bone screw.

11. The system of claim 1, wherein the bone screws are made of metal or ceramic.

12. A system for fixation of bone fragments comprising a bone plate with a plurality of conical plate holes tapering toward a bone contact surface and at least two bone screws for anchoring the bone plate to a bone, each said screw having a conical head with a structured lateral outside surface, said head shaped to match the plate holes and used in insertion into said holes, the bone screws further comprising a threaded shank for anchoring into the bone, wherein the structured lateral outside surface has a greater hardness than portions of the bone plate located adjacent the conical plate holes and wherein the bone plate is made of one of:
a polyacrylic ether ketone (PAEK) having a rupture elongation of 40 to 70% and a Young's modulus of 3,000 to 6,000 N/mm$^2$;
a polyether ether ketone (PEEK) having a rupture elongation of 40 to 70% and a Young's modulus of 3,000 to 6,000 N/mm$^2$;
a polysulfone having a rupture elongation of 80 to 120% and a Young's modulus of 2,000 to 3,500 N/mm$^2$;
a Liquid Crystal Polymer (LCP) having a rupture elongation of 1.5 to 2.5% and a Young's modulus of 5,000 to 20,000 N/mm$^2$;
a polyoxymethylene (POM) having a rupture elongation of 10 to 50% and a Young's modulus of 2,000 to 3,500 N/mm$^2$; or
a polyphenylene sulfide (PPS) having a rupture elongation of 0.2 to 1% and a Young's modulus of 12,000 to 20,000 N/mm$^2$.

13. The system of claim 12, wherein the bone plate is made of a polysulfone with a rupture elongation of 80 to 120% and with a Young's modulus of 2,000 to 3,500 N/mm$^2$.

14. The system of claim 12, wherein the bone plate is made of a Liquid Crystal Polymer (LCP) with a rupture elongation of 1.5 to 2.5% and with a Young's modulus of 5,000 to 20,000 N/mm$^2$.

15. The system of claim 12, wherein the bone plate is made of polyoxymethylene (POM) with a rupture elongation of 10 to 50% and with a Young's modulus of 2,000 to 3,500 N/mm$^2$.

16. The system of claim 12, wherein the bone plate is made of a polyphenylene sulfide (PPS) with a rupture elongation of 0:2 to 1.0% and with a Young's a modulus of 12,000 to 20,000 N/mm$^2$.

17. The system of claim 1, wherein the bone plate polymer is reinforced with metal fibers, plastic fibers or carbon fibers.

18. The system of claim 5, wherein the bone screw head coating has a hardness of 1,000 to 5,000 HV.

19. The system of claim 10, wherein the structure running transversely to the longitudinal axis of the bone screw comprises circumferential ribs.

* * * * *